US00PP11364P

United States Patent [19]

Heims

[11] Patent Number: Plant 11,364

[45] Date of Patent: Apr. 25, 2000

[54] *OMPHALODES CAPPADOCICA* PLANT NAMED 'PARISIAN SKIES'

[75] Inventor: Dan M. Heims, Portland, Oreg.

[73] Assignee: Terra Nova Nurseries, Inc., Portland, Oreg.

[21] Appl. No.: 09/107,864

[22] Filed: Jun. 30, 1998

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Wendy A Baker
*Attorney, Agent, or Firm*—Klarquist Sparkman Campbell Leigh & Whiston, LLP

[57] ABSTRACT

A new and distinct form of Omphalodes plant characterized by unique flower color.

1 Drawing Sheet

The present invention relates to a new and distinct sport of Omphalodes which originated as a tissue culture mutation of *Omphalodes cappadocica* 'Starry Eyes' (unpatented).

This new Omphalodes is a result of a tissue culture sport at Terra Nova Nurseries, Inc., in Canby, Oreg. This sport was selected from a large group of clonally propagated *Omphalodes cappadocica* 'Starry Eyes' plants that were retained to observe habit and to compare with the new variety. The new variety has been reproduced only by asexual propagation (tissue culture). Each of the progeny exhibits identical characteristics to the original plant and is unlike any Omphalodes offered by any American nursery or book known to me as evidenced by the following characteristic: Unique flower color. Asexual propagation by tissue-culture as done in Tigard, Oreg., shows that the foregoing characteristics and distinctions come true to form and are established and transmitted through suceeding propagations. Omphalodes is in the family Boraginaceae.

BRIEF DESCRIPTION OF THE DRAWING

The drawing shows plant in full bloom in April in Oregon. The drawing depicts the plant as true to type as is photographically possible.

DETAILED PLANT DESCRIPTION

The following is a detailed description of the new Omphalodes based on observations of specimens in Canby, Oreg. The color descriptions are all based on *The Royal Horticultural Society Colour Chart* and the *American Rhododendron Society* publication: *A CONTRIBUTION TOWARD STANDARDIZATION OF COLOR NAMES IN HORTICULTURE.*

Foliage:
- *Type.*—Herbaceous.
- *Shape.*—Ovate to cordate.
- *Length.*—8–8.5 cm.
- *Width.*—5 cm.
- *Petiole length.*—7–8 cm.
- *Margins.*—Entire, ciliate.
- *Apex.*—Acute-acuminate.
- *Base.*—Obtuse.
- *Texture.*—Finely pilose.
- *Petiole texture.*—Sericeous.
- *Leaf arrangement.*—Basal clump.
- *Venation.*—Camptodromus, lateral veins prominent.

Size:
- *Height.*—20 cm (2-year-old plant in Oregon).
- *Width.*—40 cm (2-year-old plant in Oregon).

Flower:
- *Petal count.*—5 petals.
- *Petal shape.*—Rounded.
- *Flower type.*—Complete, rotate (wheel-shaped); calyx 5-parted.
- *Flower size.*—0.9 cm to 1 cm (from petal tip to petal tip).
- *Flower number.*—10–15 per raceme.
- *Flower stem girth.*—3 mm tapering to 1 mm.
- *Flower stem texture.*—Sericeous.
- *Height of plant in bloom.*—21 cm.
- *Blooming habit.*—Racemes, no tendency towards fasciation observed.
- *Bloom period.*—In Oregon, early March to late April, some rebloom in fall.

Disease: Plants grown in Canby, Oreg., show no sign of disease susceptibility except for root rot when grown under wet conditions.

Color characteristics:
- *Foliage.*—Mature leaves upper surface. Spring: R.H.S.143 B Yellow Green Group (Strong Yellow Green ARS). Mature leaves upper surface, summer through winter: R.H.S. 146A Yellow Green Group (Moderate Olive Green ARS). Mature leaves lower surface: R.H.S. 147C Yellow Green Group (Moderate Yellow Green ARS).
- *Flowers.*—Buds are R.H.S. 76A, Purple Group (Light Purple ARS) open to R.H.S. 101A, Blue Group (Vivid Purplish Blue ARS) and fade to 100B, Blue Group (Strong Blue).
- *Flower stem.*—R.H.S. 144A Yellow Green Group.

DESCRIPTION OF ORIGINAL PLANT

*Omphalodes cappadocica* 'Starry Eyes' is identical in all aspects except for the flower color. *Omphalodes cappadocica* 'Starry Eyes' has white to pink centered blooms with a brilliant blue edge, whereas *Omphalodes cappadocica* 'Parisian Skies' has even, bright blue coloring throughout the flower.

I claim:

1. A new and distinct hybrid of Omphalodes plant substantially as shown and described, characterized by its unique flower color.

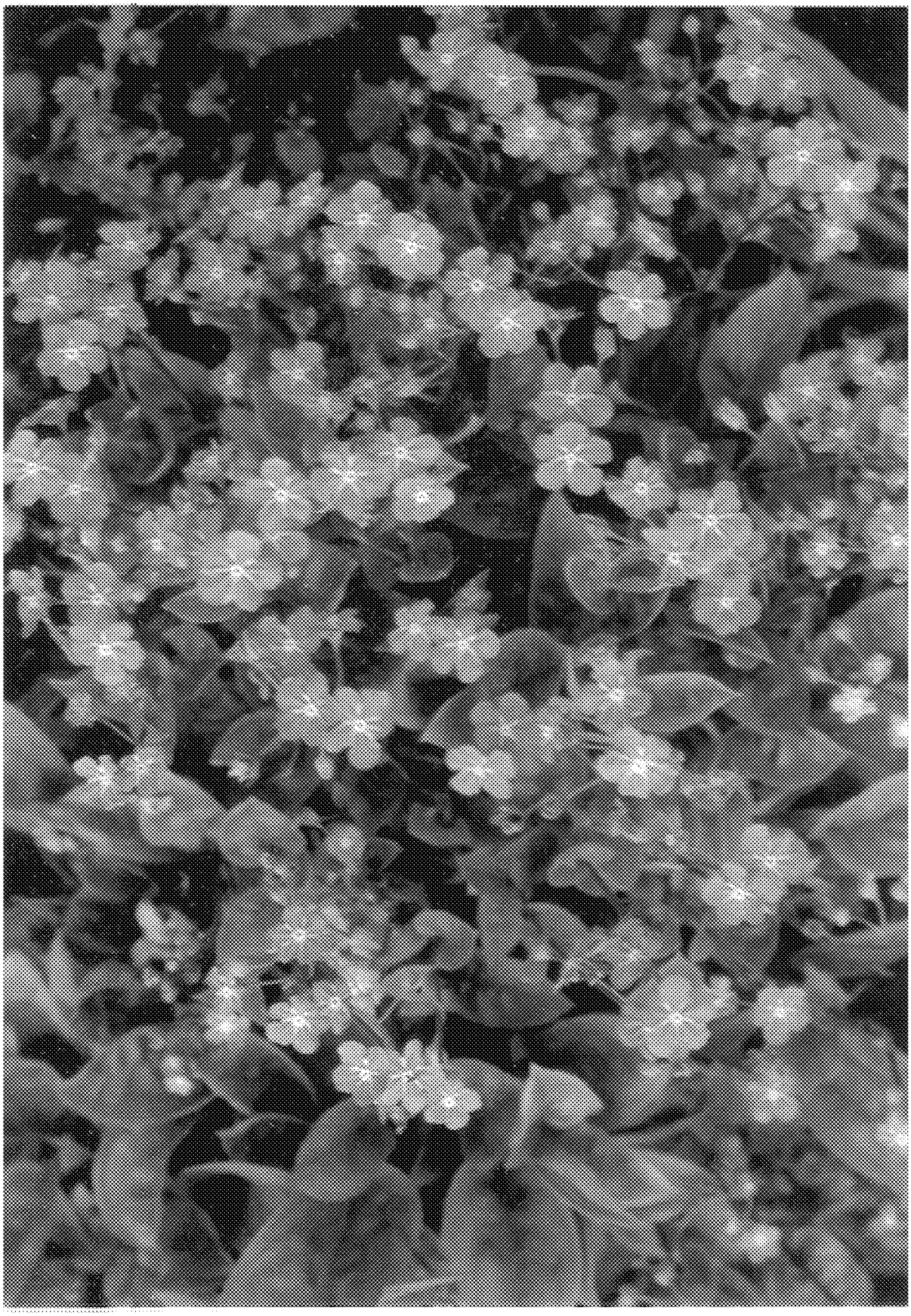

* * * * *